United States Patent
Hutchison

(10) Patent No.: US 7,264,862 B2
(45) Date of Patent: Sep. 4, 2007

(54) SOILING DETECTOR FOR FABRICS

(75) Inventor: Robert D. Hutchison, Buchanan, VA (US)

(73) Assignee: Mohawk Brands Inc., Wilmington, DE (US)

( * ) Notice: Subject to any disclaimer, the term of this patent is extended or adjusted under 35 U.S.C. 154(b) by 337 days.

(21) Appl. No.: 10/612,284

(22) Filed: Jul. 3, 2003

(65) Prior Publication Data

US 2005/0003138 A1    Jan. 6, 2005

(51) Int. Cl.
*B32B 3/02* (2006.01)
*B32B 33/00* (2006.01)

(52) U.S. Cl. .......................... 428/97; 428/92; 428/913; 442/308; 442/309; 442/189; 442/192

(58) Field of Classification Search .................. 428/97, 428/92, 913; 442/308, 309, 189, 192; 15/208, 15/210, 215, 217, DIG. 11
See application file for complete search history.

(56) References Cited

U.S. PATENT DOCUMENTS

| | | | |
|---|---|---|---|
| 3,989,866 A * | 11/1976 | Eskridge et al. | 428/92 |
| 4,298,282 A | 11/1981 | Williams | |
| 4,877,669 A * | 10/1989 | Endrenyi et al. | 428/88 |
| 4,961,243 A * | 10/1990 | Barber | 15/230 |
| 5,208,107 A | 5/1993 | Yeh et al. | |
| 5,380,592 A | 1/1995 | Tung | |
| 5,413,857 A * | 5/1995 | Hagen et al. | 428/357 |
| 5,668,632 A | 9/1997 | Kobayashi et al. | |
| 6,048,615 A | 4/2000 | Lin | |
| 6,447,903 B1* | 9/2002 | Bernaschek | 428/376 |
| 2005/0048253 A1* | 3/2005 | Nord et al. | 428/89 |

FOREIGN PATENT DOCUMENTS

KR    9206129 B  *  7/1992

OTHER PUBLICATIONS

101 Weaves in 101 Fabrics, Textile Press, 1961, pp. 5, 22, and 46.*
Abstract of article entitled "Method for Evaluating the Soiling of Carpets from Synthetic-Fibre Yarns," Suslina et al., Tekhnologiya Legkoi Promyshlennosti, 1984, 27, No. 4/160, pp. 36-39.

* cited by examiner

*Primary Examiner*—Cheryl A. Juska
(74) *Attorney, Agent, or Firm*—Nixon & Vanderhye P.C.

(57) ABSTRACT

A fabric is formed of yarns having soiling-hiding and soiling-prone characteristics which are visually distinct one from the other in the surface of the fabric once the fabric has been soiled. The soiling-prone yarns comprise yarns formed of multi-lobal fibers or filaments where the soiling particles collect in the cavities of the lobed surfaces. Preferably, the soiling-hiding yarns are formed of hollowfil synthetic fibers or filaments. By embedding one or more yarns of the soiling-prone type in the fabric, e.g., carpet, the yarns become differentially visually distinctive relative to one another upon soiling of the fabric.

21 Claims, 4 Drawing Sheets

SOILING DETECTOR FOR FABRICS

BACKGROUND OF THE INVENTION

The present invention relates to a fabric construction and a method of constructing the fabric to enable detection of soiling of the fabric and particularly relates to fabric having a combination of yarns formed of multi-lobal fibers or filaments and so-called hollowfil fibers or filaments.

Fabrics, particularly carpets, are prone to soiling over time and usage. While carpets may be placed on a schedule for periodic cleaning, oftentimes the soiling of the carpet goes unnoticed or the cleaning is ineffective. A regular maintenance schedule, particularly for carpeting installed in commercial buildings, is a requisite to maintaining satisfactory carpet appearance, specifically since proper carpet maintenance will often prolong the life of the carpet. Ineffective cleaning, apart from unsightly aesthetics, can shorten carpet life. Consequently, there is an imperative to identify fabrics, e.g., carpeting, which have been soiled to the extent indicating a need for cleaning the fabric or to identify fabrics which have been ineffectively cleaned.

BRIEF DESCRIPTION OF THE INVENTION

In accordance with a preferred embodiment of the present invention, fabric, for example, carpeting, is manufactured having an embedded soiling detector. For clean fabrics, the soiling detector is not visually distinguishable or otherwise from the remaining portions of the fabric. Consequently, the aesthetic characteristics of the fabric, e.g., carpeting, are not diminished in any respect by embedding a soiling detector in the fabric. After the fabric has reached a point of objectionable soiling, however, the soiling detector stands out in appearance from the fabric, i.e., stands out against the background of the fabric.

To accomplish the foregoing, the soiling detector comprises one or more yarns embedded in the fabric, e.g., carpet, formed of a multi-lobal fiber or filament construction wherein the cavities of the external lobes of the fibers are prone to collect soil. Preferably, the multi-lobal yarns are provided in a very low proportion in the fabric to the remaining yarns which, in carpet construction, are preferably formed of hollowfil fibers. A hollowfil fiber or filament is typically rectilinear in cross-section having one or more elongated cavities or tubes within the interior of the fibers, the cavities or tubes containing air. The hollowfil fibers also have an exterior shape which tends to inhibit collection and retention of soiling particles in the fabric, whereas the yarn formed of multi-lobal fibers and embedded as a soiling detector or indicator in the fabric has multiple areas where soiling particles can collect and remain trapped. Thus, by using a combination of yarns, one type of which is formed of fibers not prone to collecting and retaining soiling particles, while the other type is formed of fibers prone to collecting and retaining soiling particles, the soiling particle collection and retention capacity of the yarn formed of multi-lobal fibers will stand out in appearance from the other yarns of the fabric, thus indicating a need for cleaning the fabric.

The yarns formed of multi-lobal fibers are provided preferably, in a very low proportion to the hollowfil yarns such that the soiling particle collection and retention by yarns of the multi-lobal fibers show clearly against the background of the hollowfil yarns. While the hollowfil and multi-lobal fibers of the yarns have different abilities to retain soiling particles, soiling indication is also provided by light magnification by specks of soiling particles on the yarn surfaces of the multi-lobal yarns formed of multi-lobal fibers, as compared with the minimization of the magnification of specks of soiling particles on the surfaces of hollowfil yarns by light diffraction. Consequently, it is believed that this additional soiling indicating mechanism, apart from the difference in soiling particle collection and retention of the two different types of yarns, further enhances the capacity of the combination of yarns as an indication of soiling and a practical indicator of a degree of fabric soiling necessitating cleaning.

Tri-lobal fiber forming yarns are preferable and have a hallmark characteristic in that the three lobes inherent in their construction afford cavities between the lobes prone to collect soil. Tri-lobal yarns are formed of synthetic fibers, which may include polylactic acid base, polyester, P.T.T., polypropylene, polyolefin, nylon-type 6, nylon-type 6.6, nylon-type 6.12, polyamide, viscose, extruded metal fibers and fibers based upon naturally occurring non-synthetic materials, such as milk, soy or seaweed. Hollowfil yarns may be comprised of type 6 nylon and polypropylene, particularly for carpeting and other fibers for non-carpet applications. Additionally, the hollowfil yarns may be formed of synthetic fibers, which may include polylactic acid base, polyester, P.T.T., polyolefin, nylon-type 6.6, nylon-type 6.12, polyamide, viscose, extruded metal fibers and fibers based upon naturally occurring non-synthetic materials, such as milk, soy or seaweed similarly as the tri-lobal yarns. It will also be appreciated that the soiling detector may be included as part of an aesthetic design in the fabric, i.e., a constituent of a pattern. For example, the soiling detector or indicator formed of tri-lobal yarns may be a light-colored outline around a patterned element in a carpet, such as a rose flower design.

In a preferred embodiment according to the present invention, there is provided a method of monitoring soiling in a fabric, comprising the steps of (a) providing the fabric with soiling-hiding yarns and at least one soiling-prone yarn and (b) visually distinguishing the one soiling-prone yarn and soiling-hiding yarns in the fabric as an indicator of the extent of soiling of the fabric.

In a further preferred embodiment according to the present invention, there is provided a method of monitoring soiling in a carpet, comprising the steps of (a) forming the carpet with yarns formed of hollowfil fibers and yarns formed of multi-lobal fibers to provide a carpet with visually non-distinguishable aesthetic characteristics on the technical face thereof when the carpet is clean and (b) visually distinguishing the yarns from one another in response to a soiling of the carpet.

In a further preferred embodiment according to the present invention, there is provided a fabric having a soiling indicator therein comprising predominantly soiling-hiding yarns and at least one soiling-prone yarn enabling visual distinction between the soiling-hiding and soiling-prone yarns as an indicator of the extent of soiling of the fabric.

DETAILED DESCRIPTION OF THE INVENTION

Figure 1:
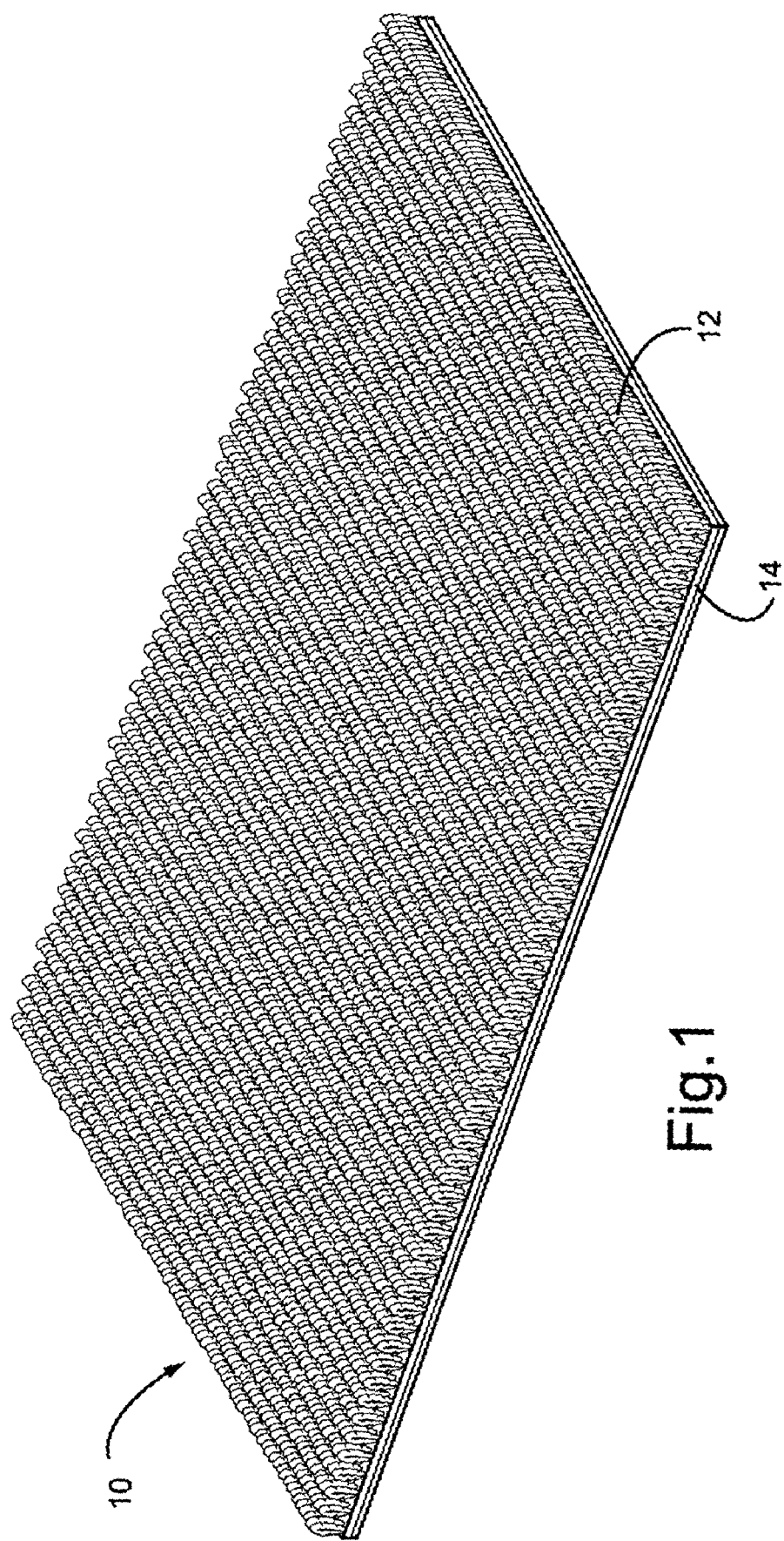
FIG. 1 is a perspective view of a portion of a clean fabric, e.g., a carpet, having a soiling indicator embedded therein in accordance with a preferred embodiment of the present invention.

Referring now to FIG. 1, there is illustrated a fabric, for example, a carpet generally indicated at 10, having a soiling indicator embedded in the fabric. In the illustrated preferred embodiment of the carpet, yarns 12 are tufted through a substrate 14, the yarns 12 forming loops on the technical face of the carpet. It will be appreciated that a tufted cut loop pile can be provided in lieu of the tufted loop pile illustrated in FIG. 1. The carpet of FIG. 1 includes one or more soiling-indicating tufted yarns embedded within the carpet which are not visually distinguishable from other soiling hiding yarns, the latter yarns forming the predominant yarns of the carpet. Thus, the carpet illustrated in FIG. 1 shows no visually distinguishing characteristics between two types of yarns, i.e., soiling hiding and soiling indicating yarns, forming the technical face of the carpet and therefore the carpet of FIG. 1 is indicating a clean carpet condition. That is, because the technical face of the carpet does not indicate soiling, the carpet is clean to the extent soiling is not objectionable.

The terms "soiling-hiding" and "soiling-prone" or "soiling-indicating" are relative terms meaning that the yarns of one category, i.e., "soiling-hiding," do not usually show the effect of dirt or soiling as the yarns of the other yarn category i.e., "soiling-prone" or "soling indicating" for the same magnitude of soiling.

Figure 2:
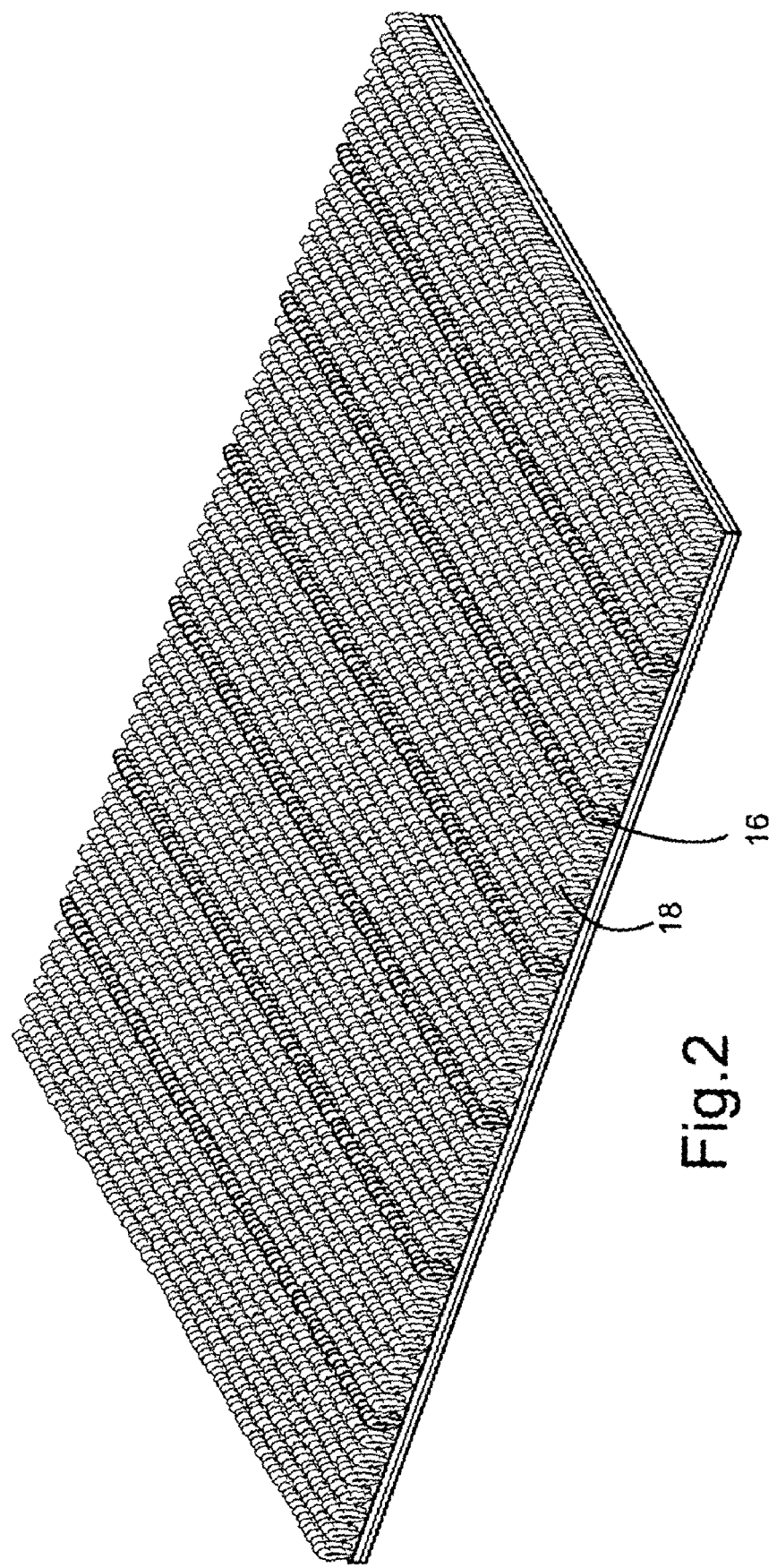
FIG. 2 is a view similar to FIG. 1 with the soiling indicator visually standing out from the technical face of the carpet.

Referring now to FIG. 2, the carpet 10 is indicating a degree of soiling, which is objectionable. In FIG. 2, the soiling-indicating yarns 16 are interspersed with soiling-hiding yarns 18 and are visible and stand out from the yarns 18. In this particular embodiment, a series of soiling-indicating yarns 16 are arranged in parallel rows in a specific portion of the fabric. For example, the rows may be arranged near the border of a carpet with a wall so that the soiling indicator is not readily observable by the general public but is observable by an individual charged with maintenance or cleaning of the carpet and who knows where on the carpet to look for an indication of soiling. That is, one or more rows of soiling prone yarns 16, i.e. yarns retaining soiling particles, are preferably provided in the carpet adjacent an obscure region of the carpet whereby the soiling indication is observable by all but which visual differentiation of the yarns indicates to the individual charged with maintaining or cleaning a carpet the need for cleaning.

Figure 4:
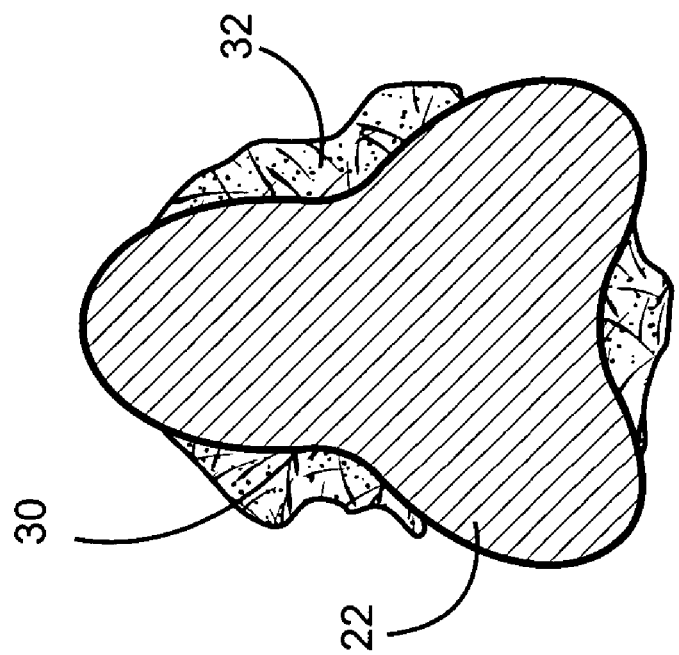
FIGS. 3 and 4 are enlarged cross-sectional views illustrating hollowfil and tri-lobal fibers, respectively, employed in the yarns of the fabric having the soiling indicator hereof.
Figure 3:
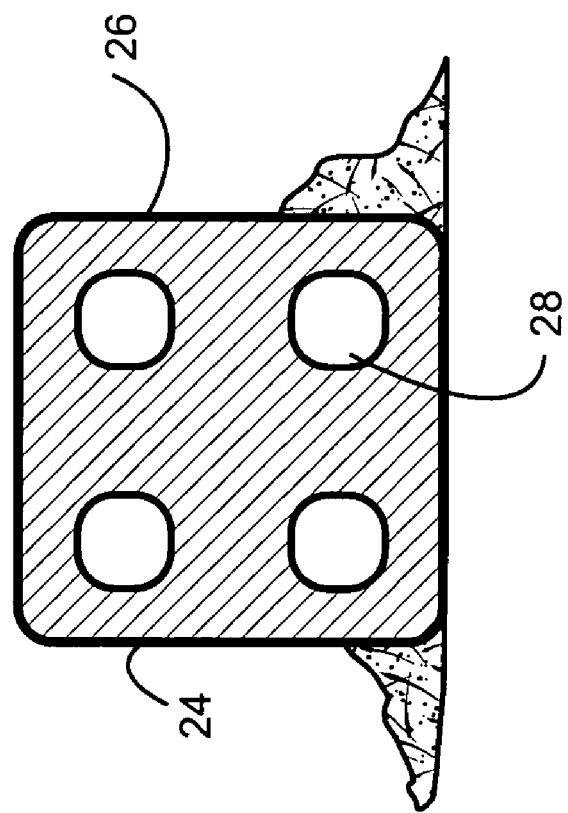

Referring now to FIGS. 3 and 4, the fabric is formed of a combination of yarns 16 formed of soiling-prone fibers 22 and yarns 18 formed of soiling-hiding fibers 24. It is the combination of the yarns formed of soiling-hiding fibers 24 and soiling-prone fibers 22 which affords the distinctive visual contrast between the two types of yarns in the fabric giving an indication of an objectionable magnitude of soiling of the fabric. The hollowfil fibers 18 are formed of a synthetic material and generally have sides 26 of rectilinear external shape in cross-section with one or more tubes or passages 28 extending through the interior of the yarns. Those passages typically contain air.

Figure 5:
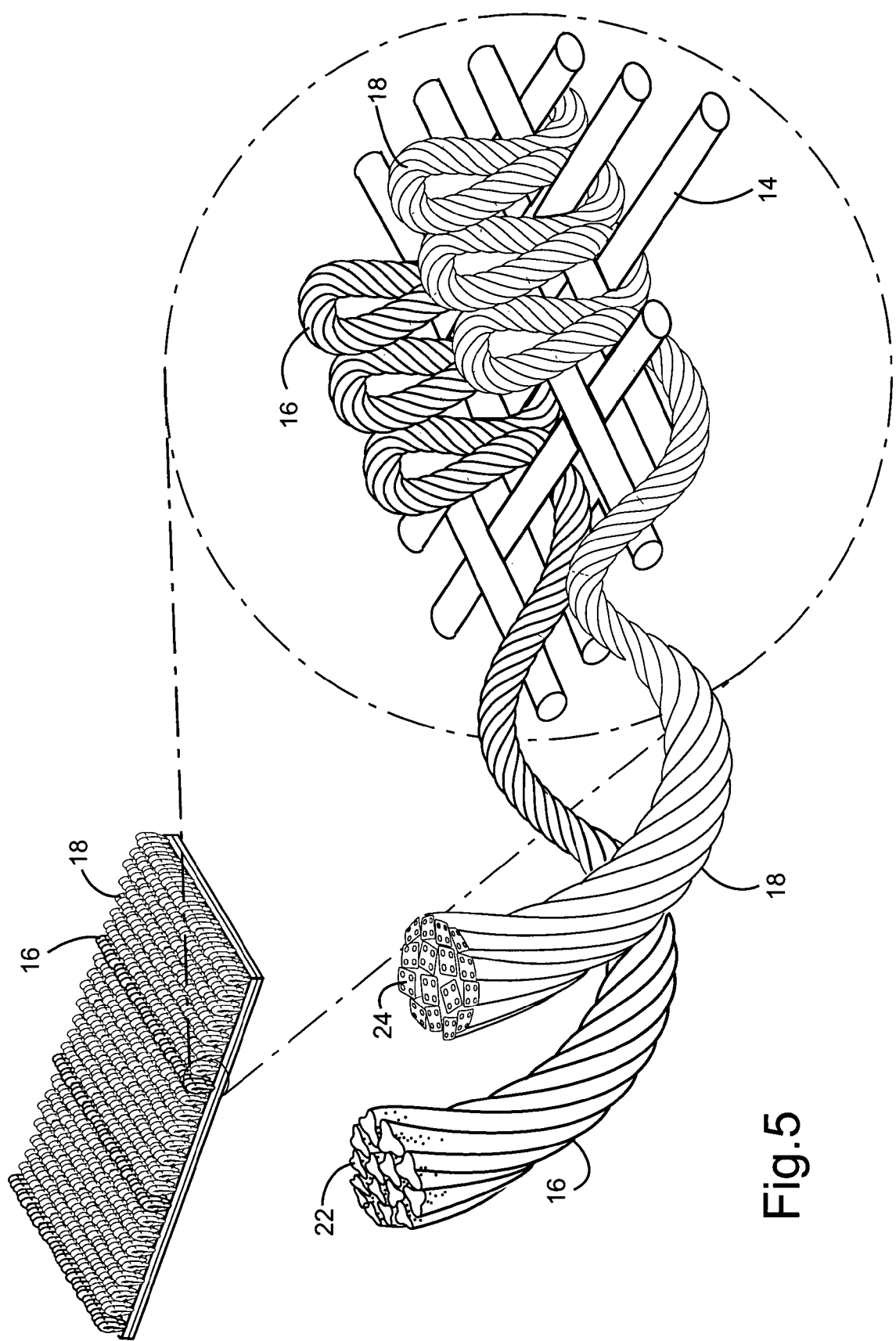
FIG. 5 is an enlarged perspective view of adjoining yarns in a carpet made of the fibers illustrated in FIGS. 3 and 4, and incorporating the soiling indicator hereof.

Referring to FIGS. 4 and 5, fibers 22 forming the soiling-indicating yarns 16 preferably have a multi-lobal cross-sectional external configuration, for example, the illustrated tri-lobal configuration. Because of the nature of the sides or legs 30 of the multi-lobal fibers 22 forming the soil-indicating yarns, soiling particles, e.g. particles 32, tend to accumulate along the cavities of the lobes of the yarn. Thus, the soiling particles collect and are retained within the cavities of the multi-lobal fibers (when twisted into yarns 16) to a greater extent than soiling particles are collected and retained in the yarns formed of hollowfil fibers 24 illustrated in FIG. 3. Consequently, by embedding one or more of the soiling-prone yarns 16 in the fabric for exposure through the technical face of a carpet, the soiling-prone yarn will become visually distinct relative to the background of the predominantly soiling-hiding yarns 18, affording an indication that the fabric, e.g., carpet, has become soiled to the extent cleaning is desirable.

The multi-lobal fibers 22 forming the yarn 16 may be formed of various synthetic materials. For example, the preferred tri-lobal fibers 22 forming yarns 16 may be formed of polylactic acid base, polyester, polypropylene, polyolefin, nylon, polyamide, extruded metal fibers or fibers based upon naturally occurring non-synthetic material. The hollowfil yarns may be comprised of Type 6 nylon and polypropylene, for example, for use in carpeting.

Additionally, the soiling indication is enhanced by a light magnification of the multi-lobal yarns by specks of soiling particles on the lobe surfaces. This is in contrast to the lack of any substantial magnification of specks of soiling particles on the surfaces of the hollowfil yarns by light diffraction. Consequently, not only is the soiling indication afforded by the collection and retention of soiling particles by the multi-lobal yarns in comparison with the comparatively reduced collection and retention of soiling particles by the hollowfil yarns, but the indication is enhanced by the light magnification of the soiling particles collected and retained in the cavities of the multi-lobal yarns.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of monitoring soiling in a fabric, comprising the steps of:
   (a) providing the fabric with soiling-hiding yarns and at least one soiling-prone yarn that is not visually distinguishable from the soil-hiding yarns before the fabric has been soiled, including spacing the soiling-prone yarn or groups thereof from one another in at least selected areas of the fabric; and
   (b) visually distinguishing the one soiling-prone yarn and soiling-hiding yarns in the fabric, after the fabric has been soiled, as an indicator of the extent of soiling of the fabric.

2. A method according to claim 1 wherein the soiling-hiding yarns include yarns formed of hollowfil fibers.

3. A method according to claim 1 wherein the soiling-prone yarns include yarns formed of multi-lobal fibers.

4. A method according to claim 1 wherein the soiling-prone yarns include yarns formed of tri-lobal fibers.

5. A method according to claim 1 wherein the soiling-hiding yarns include yarns formed of hollowfil fibers and the soiling-prone yarns include yarns formed of multi-lobal fibers.

6. A method according to claim 1 including forming the fabric using a plurality of soiling-prone yarns.

7. A method according to claim 1 including forming the fabric with predominately soiling-hiding yarns.

8. A method according to claim 1 wherein said soiling-prone yarn comprises a synthetic fiber.

9. A method according to claim 1 wherein said soiling-prone yarn comprises one of a polylactic acid base, polyester, polypropylene, polyolefin, nylon, polyamide, or extruded metal fibers or fibers based upon naturally occurring non-synthetic material.

10. A method according to claim 1 wherein said soil-hiding yarns comprise a synthetic fiber.

11. A method according to claim 10 wherein said soiling-prone yarn comprises one of a polylactic acid base, polyester, polypropylene, polyolefin, nylon, polyamide or extruded metal fibers or fibers based upon naturally occurring non-synthetic materials.

12. A method according to claim 1 wherein the fabric comprises a carpet and including causing the soiling-prone yarn to visually stand out from the soil-hiding yarns in the technical face of the carpet in response to a soiling of the carpet, thereby visually indicating a need to clean the carpet.

13. A method according to claim 1 wherein: (1) a soiling-hiding yarn has a chemical composition and a cross-section, and (2) at least one soiling-prone yarn has the same chemical composition as the soiling-hiding yarn and a different cross-section.

14. A method of monitoring soiling in a carpet, comprising the steps of:
(a) forming the carpet with yarns formed of hollowfil fibers and yarns formed of multi-lobal fibers to provide a carpet with visually non-distinguishable aesthetic characteristics on the technical face thereof when the carpet is clean, including spacing the yarns formed of multi-lobal fibers from one another in at least selected areas of the fabric; and
(b) visually distinguishing the yarns from one another in response to a soiling of the carpet.

15. A fabric having a soiling indicator therein comprising predominantly soiling-hiding yarns and at least one soiling-prone yarn enabling visual distinction between the soiling-hiding and soiling-prone yarns as an indicator of the extent of soiling of the fabric and wherein said fabric has a face with said soiling-hiding yarns and said one soiling-prone yarn visually exposed in said face and visually indistinguishable from one another absent soiling of the fabric and wherein the at least one soiling-prone yarn is in at least selected areas of the fabric and is spaced from other soiling-prone yarns or groups thereof.

16. A fabric according to claim 15 wherein said one yarn is formed of synthetic multi-lobal fibers.

17. A fabric according to claim 16 wherein said one yarn is formed of tri-lobal fibers.

18. A fabric according to claim 16 wherein said predominantly soiling-hiding yarns are formed of synthetic hollowfil fibers.

19. A fabric according to claim 15 comprising a carpet, said soiling-hiding yarns and said one soiling-prone yarn visually appearing in the technical face of the carpet.

20. A fabric according to claim 19 wherein said soiling-hiding yarns and said one soiling-prone yarn are tufted into a substrate forming part of the carpet.

21. A fabric according to claim 15 wherein: (1) a soiling-hiding yarn has a chemical composition and a cross-section, and (2) at least one soiling-prone yarn has the same chemical composition as the soiling-hiding yarn and a different cross-section.

\* \* \* \* \*